(12) United States Patent
Campbell et al.

(10) Patent No.: US 12,397,297 B2
(45) Date of Patent: Aug. 26, 2025

(54) SLIDE PREPARATION METHODS AND APPARATUS

(71) Applicant: ZOMEDICA INC., Ann Arbor, MI (US)

(72) Inventors: William Eugene Campbell, Marietta, GA (US); Negin Ghassemian, Smyrna, GA (US)

(73) Assignee: Zomedica Inc., Ann Arbor, MI (US)

( * ) Notice: Subject to any disclaimer, the term of this patent is extended or adjusted under 35 U.S.C. 154(b) by 298 days.

(21) Appl. No.: 17/977,460

(22) Filed: Oct. 31, 2022

(65) Prior Publication Data

US 2024/0139744 A1    May 2, 2024

(51) Int. Cl.
*G02B 21/34* (2006.01)
*B01L 3/00* (2006.01)
*A61B 5/15* (2006.01)

(52) U.S. Cl.
CPC .......... *B01L 3/50825* (2013.01); *G02B 21/34* (2013.01); *A61B 5/15003* (2013.01); *A61B 5/150389* (2013.01); *A61B 5/150732* (2013.01)

(58) Field of Classification Search
CPC .... B01L 9/06; B01L 9/52; B01L 9/523; B01L 9/527; B01L 2300/0822; G01N 2035/00138; G01N 2035/00148; G02B 21/34
See application file for complete search history.

(56) References Cited

U.S. PATENT DOCUMENTS

| | | | | |
|---|---|---|---|---|
| 4,516,522 A | * | 5/1985 | Drury | ................. G01N 1/2813 118/100 |
| 2015/0056695 A1 | * | 2/2015 | Nordberg | ............... B01L 3/502 422/500 |

* cited by examiner

*Primary Examiner* — Jill A Warden
*Assistant Examiner* — Dwayne K Handy
(74) *Attorney, Agent, or Firm* — Standley Law Group LLP; Jeffrey S. Standley; Bryan P. Finneran

(57) ABSTRACT

Various examples are provided related to slide preparation. In one example, a slide preparation apparatus includes a support surface, an upper surface opposite the support surface, and a sample tube holder. The upper surface can include a slide channel extending to a stop, a fiducial mark disposed in the slide channel, and a support bar extending across the slide channel. The sample tube holder can secure a sample tube in a vertical position adjacent to an end of the upper surface adjacent to the stop. When a syringe is supported by a sample tube positioned in the sample tube holder, a needle of the syringe can be aligned with the fiducial mark when it is seated in a guide groove of the support bar.

20 Claims, 5 Drawing Sheets

SLIDE PREPARATION METHODS AND APPARATUS

BACKGROUND

Microscope slides are prepared by hand for examination under a microscope. Positioning of the sample on the slide is an important aspect for automated processing. Consistency of sample position can facilitate smearing, treatment and examination of liquid or other samples. This can be especially true for automated slide processing.

SUMMARY

Aspects of the present disclosure are related to slide preparation. In one aspect, among others, a slide preparation apparatus comprises a support surface; an upper surface opposite the support surface; and a sample tube holder affixed to an end surface of the slide preparation apparatus. The upper surface can comprise a slide channel extending from a first end of the upper surface to a stop adjacent to a second end of the upper surface; a fiducial mark disposed in the slide channel, the fiducial marker located a defined distance from the stop; and a support bar extending across the slide channel, the support bar comprising a guide groove aligned with the fiducial marker. The sample tube holder can be configured to secure a sample tube in a vertical position adjacent to the second end of the upper surface.

In one or more aspects, the fiducial mark, guide groove and sample tube holder can be linearly aligned along a length of the slide channel. The fiducial mark, guide groove and sample tube holder can be linearly aligned along a center of the slide channel. The stop can extend across a width of the slide channel. The width of the slide channel can correspond to a width of a slide. The slide channel can comprise sidewalls on opposite sides of the slide channels, the sidewalls configured to constrain a slide in alignment with the fiducial mark, guide groove and sample tube holder. The support bar can extend across the slide channel over the sidewalls, the support bar positioned at a height corresponding to a thickness of the slide. The guide grove can be on a side of the support bar adjacent to the fiducial mark. An upper surface of the support bar can comprise a rounded portion extending across the side of the support bar adjacent to the fiducial mark.

In various aspects, the fiducial mark can define a target location for deposition of a sample on a slide inserted in the slide channel. The fiducial mark can be visible through the slide inserted in the slide channel. The fiducial mark can comprise a depression formed in a bottom surface of the slide channel. The sample tube holder can comprise a cylindrical chamber sized to receive a sample tube. The sample tube can be a blood collection tube. The sample tube holder can comprise a structure configured to support the sample tube. The structure can extend inward from a side of the cylindrical chamber. The structure can be a tab extending inward to a center of the cylindrical chamber. The structure can extend across the cylindrical chamber. The sample tube holder can comprise at least one opening extending through a side of the cylindrical chamber providing visual access to the sample tube. In some aspects, a needle of a syringe supported by a sample tube positioned in the sample tube holder can be aligned with the fiducial mark when the needle is seated in the guide groove of the support bar.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1A:
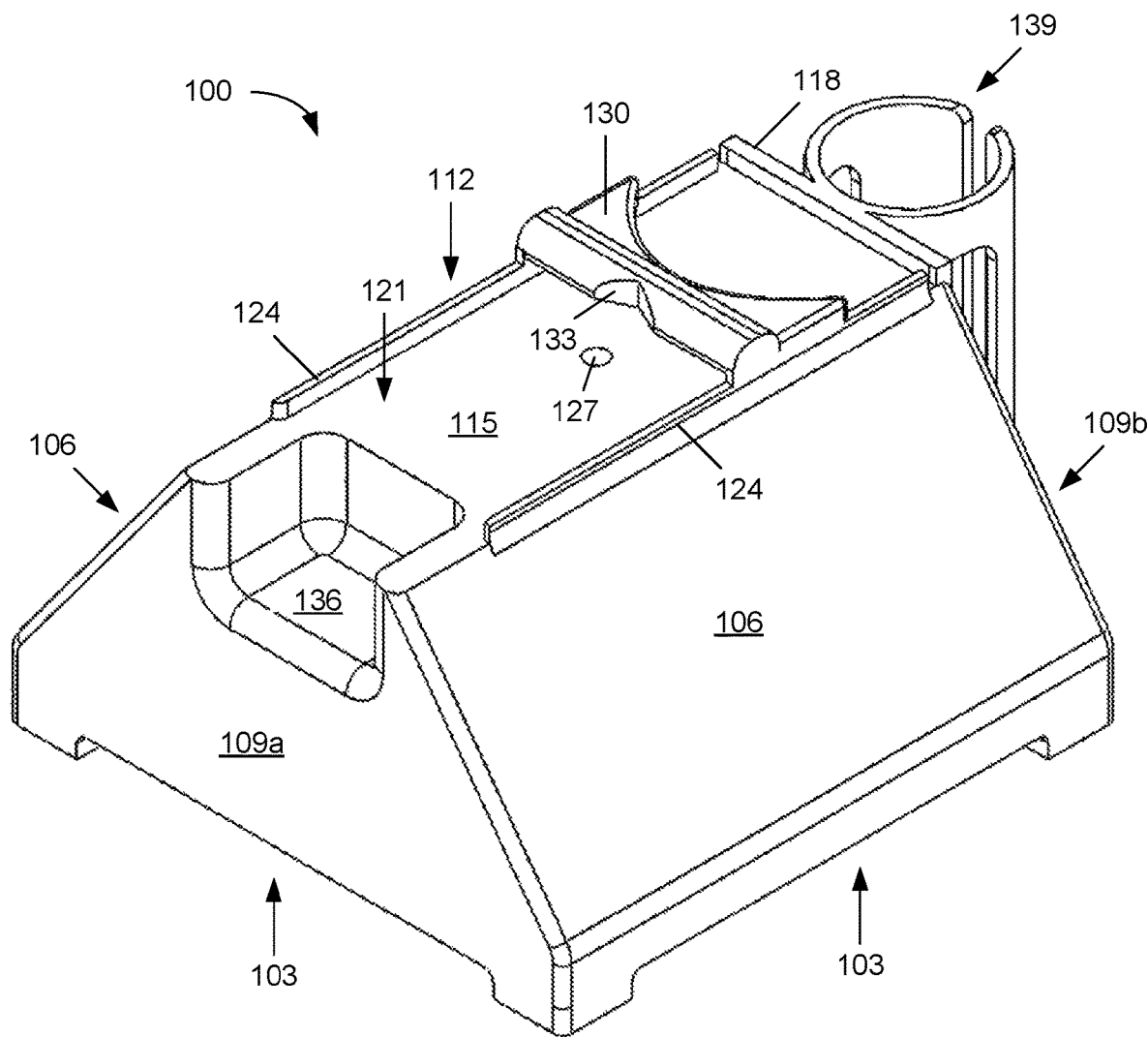
FIGS. 1A-1C illustrate an example of a slide preparation apparatus, in accordance with various embodiments of the present disclosure.

Disclosed herein are various examples related to slide preparation. Reference will now be made in detail to the description of the embodiments as illustrated in the drawings, wherein like reference numbers indicate like parts throughout the several views.

Figure 1B:
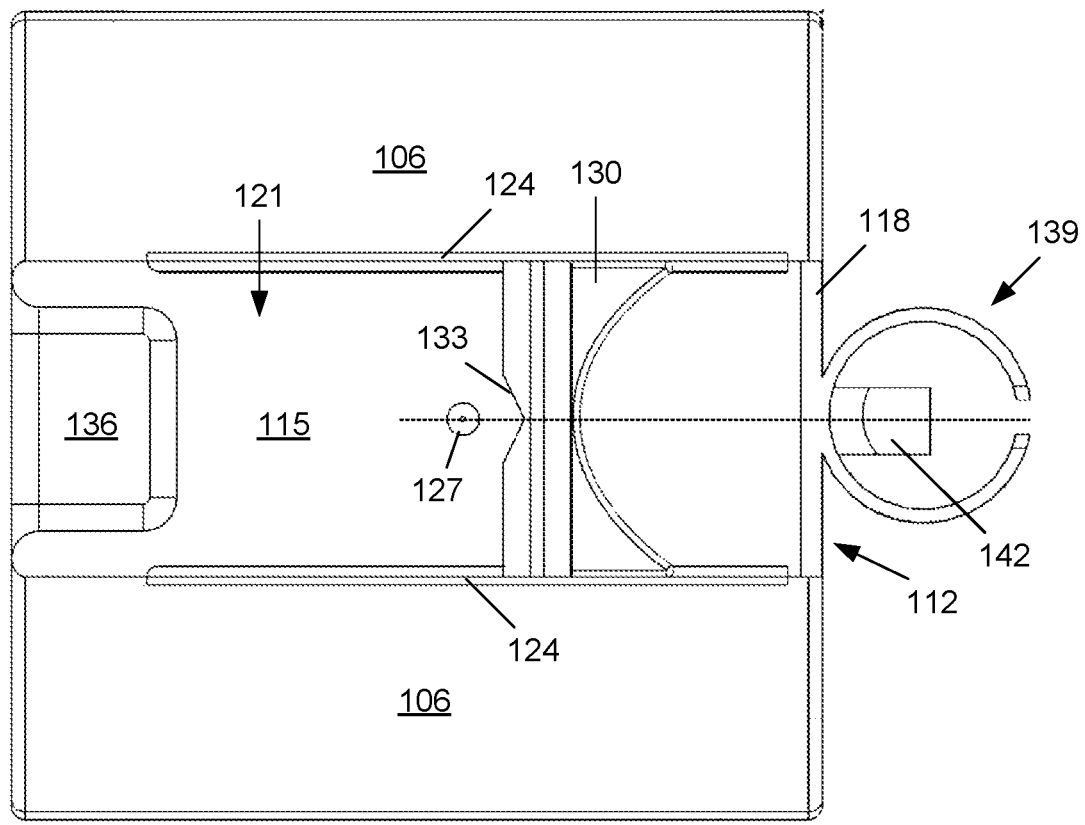
Figure 1B:
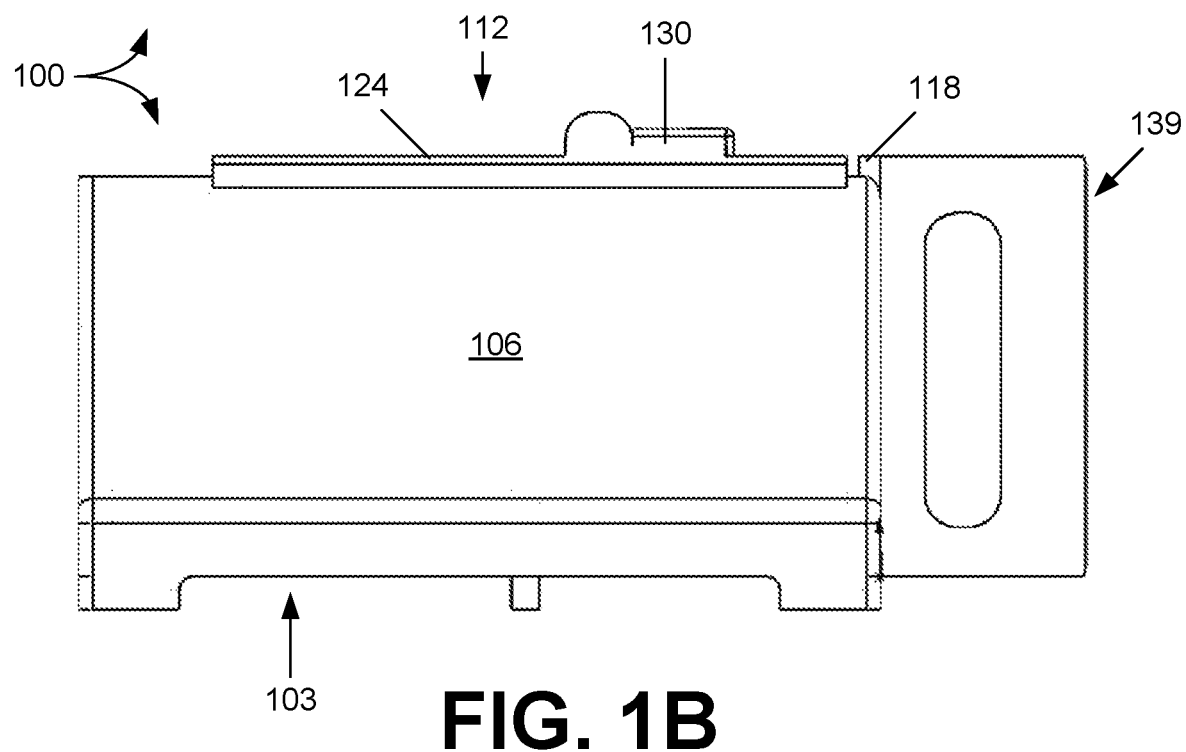
Figure 1C:
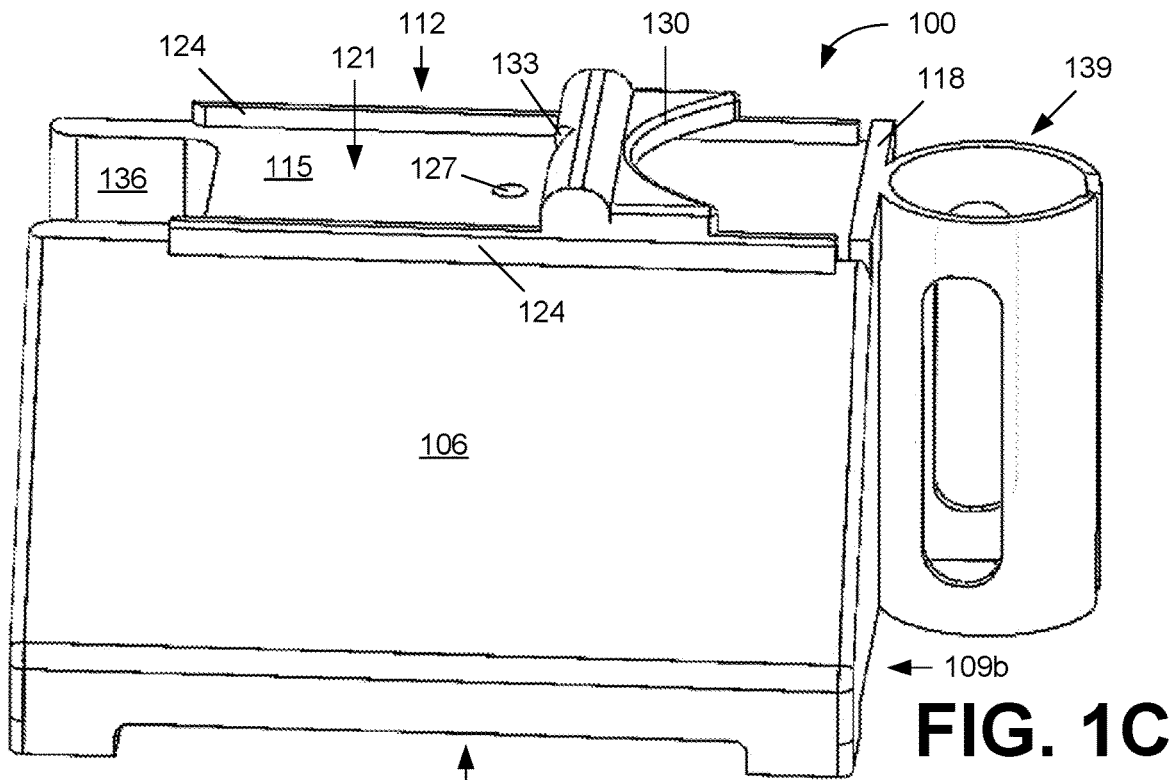

Referring to FIGS. 1A-1C, shown is an example of a slide preparation apparatus 100 that can be used by a user for placement of a sample on a slide. FIGS. 1A and 1C are perspective views of the slide preparation device 100, and FIG. 1B includes top and side views of the slide preparation device 100. As illustrated in these views, the slide preparation apparatus 100 comprises a support surface 103 on the bottom, side surfaces 106, end surfaces 109, and an upper surface 112 configured to assist with preparation of slides. The support surface 103 is configured to provide a stable base for the apparatus 100. The support surface 103 can include feet or pads distributed to support the slide preparation apparatus 100 when placed on a surface for use. As shown in FIG. 1A, feet can be located on corners of the support surface 103, which can be extended to avoid tipping of the apparatus 100 during use.

Opposite the support surface 103 is the upper surface 112, which is configured to receive a slide for preparation. The upper surface 112 can comprise a slide channel 115 extending from a first end of the upper surface 112 to a stop 118 adjacent to a second end of the upper surface 112. The slide channel 115 can be sized to receive the slide and secure it in alignment with other features of the slide preparation apparatus 100. For example, the width of the slide channel 115 corresponds to the width of the slide with tolerance allowing the slide to be inserted and removed from the slide channel 115. The slide channel 115 comprises a bottom surface 121 and sidewalls 124 defining the channel 115. The sidewalls 124 can extend along the entire length of the slide channel 115 (across the slide preparation apparatus 100) or can extend along a portion of the length of the slide channel 115, as shown in FIGS. 1A-1C.

The slide channel 115 is open at one end of the slide preparation apparatus 100 allowing the slide to be positioned within the slide channel 115. A stop 118 at the other end of the slide channel 115 limits insertion of the slide in the channel 115. In some implementations, the length of the slide channel 115 from the stop 118 to the end of the slide preparation apparatus 100 may be less than a length of the slide. With the slide inserted in the slide channel 115 and engaged with the stop 118, the end of the inserted slide may extend beyond the end surface 109a of the apparatus 100. The stop 118 can extend across the width of the slide channel 115 between the sidewalls 124 or can be less than the width of the channel 115. For example, the stop 118 can comprise one or more tabs or shoulders extending upward from the bottom surface 121 that limit the movement of the slide through the slide channel 115. The stop 118 can be located adjacent to an end of the slide preparation apparatus 100. For example, the stop 118 can extend across the end of the slide channel 115 along the end surface 109b of the apparatus 100. In some implementations, the stop 118 position may be adjustable to account for different slide dimensions.

The slide channel 115 is open along the top to allow access to the surface of the slide for deposition of a sample. A fiducial mark 127 can be provided in the channel to indicate where a sample should be positioned on a slide positioned in the slide channel 115. The fiducial mark 127 can be a defined length from the stop 118 and can be substantially centered between the sidewalls 124 of the slide channel 115 to indicate a preferred sample placement location. The fiducial mark 127 can be visible to a user of the slide preparation apparatus 100 through a transparent or semi-transparent slide positioned in the slide channel 115. The fiducial mark 127 can be formed in the bottom surface 121 of the slide channel 115 with one or more color, texture, geometry, etc. For example, the fiducial mark 127 can be a circular depression or other patterned depression in the bottom surface 121. The fiducial mark 127 can be colored or tinted to increase the visibility of the fiducial mark 127. In other implementations, the fiducial mark 127 can be printed or embossed on the bottom surface 121 with one or more color, texture, geometry, etc.

A support bar 130 can extend across a portion of the slide channel 115 at a height that allows the slide to pass under the support bar 130. The support bar 130 can extend between the sidewalls 124 of the slide channel 115 at a height of about the thickness of the slide with tolerance allowing the slide to be inserted and removed from the slide channel 115. The support bar 130 can help hold the slide in position against the bottom surface 121 of the slide channel 115. As shown in FIGS. 1A-1C, the support bar 130 can extend across a portion of the slide channel 115 between the fiducial mark 127 and the end of the slide channel 115. The support bar 130 can comprise a first side adjacent to the fiducial mark 127 and a second side opposite the first side.

The first side of the support bar 130 comprises a guide grove 133 that can be positioned with respect to the fiducial mark 127. For example, the guide groove 133 can facilitate alignment of a syringe needle with the fiducial mark 127 for deposit of a sample on the slide. The top of the support bar 130 (opposite the slide channel 115) can include a rounded portion as seen in the side view of FIG. 1B, which can aid in positioning of the needle over the fiducial mark 127. The second side of the support bar 130 can be separated from the first side by a width that allows the stop 118 to be accessible for visual confirmation of engagement of the slide with the stop 118, or the second side can extend to the end of the slide channel 115. In FIGS. 1A-1C, the second side of the support bar 130 is curved to allow visual access to the stop 118. In other embodiments, the support bar 130 can extend from the first side to the end of the slide channel 115. where the second side can be aligned with the end surface 109b of the slide preparation apparatus 100.

The end surfaces 109 and side surfaces 106 of the slide preparation apparatus 100 extend between the upper surface 112 and the support surface 103. The end and side surfaces 109 and 106 can extend vertically and/or at an angle between the upper and support surfaces 112 and 103 depending on the surface configurations. As illustrated in FIG. 1A, the support surface 103 can be larger than the upper surface 112 for stability, with the side surfaces 106 extending between the two at a fixed angle. The side and/or end surfaces 106/109 can include text, logos, designs, or other embellishments. For example, a product name can be formed or printed on one or more of the side surfaces 106 and/or end surfaces 109.

The end surfaces 109 can extend vertically between the upper and support surfaces. The end surface 109a at the open end of the slide channel 115 (opposite the stop 118) can include a cavity 136 that extends into the slide preparation apparatus 100 from the end surface 109a below the slide channel 115. The cavity 136 can provide space for gripping the slide during insertion into or removal from the slide channel 115. As shown in FIG. 1B, the width of the cavity 136 can be less than the width of the slide channel 115 so that support of the slide is provided over the full length of the slide channel 115. The depth of the cavity 136 can be varied to provide adequate access to the end of the slide for gripping.

The slide preparation apparatus 100 also includes a sample tube holder 139 affixed to an end surface 109b adjacent to the stop 118 of the slide channel 115. The sample tube holder 139 can be configured to secure a sample tube in a vertical position adjacent to the end of the slide channel 115 adjacent to the stop 118. The sample tube holder 139 can be permanently affixed to the end surface 109a or can be detachably attached to the end surface 109a of the slide preparation assembly 100. The sample tube holder 139 can comprise a cylindrical chamber sized to receive a sample tube. The sample tube can be a blood collection tube or other tube suitable for collection of blood, cytoplasma, or other fluids. As seen in the top view of FIG. 1B, the sample tube holder 139 comprises a structure 142 that extends inward from a side of the cylindrical chamber to support the sample tube. The structure 142 can be a tab this extends toward or across the center of the cylindrical chamber or can be a bar, circular base or endcap that extends across the cylindrical chamber. The sample tube holder 139 can also include one or more openings extending through a side of the cylindrical chamber to provide visual access to the sample tube in the holder 139.

As illustrated by the dashed line in the top view of FIG. 1B, the fiducial mark 127, guide groove 133 and sample tube holder 139 can be linearly aligned along a length of the slide channel 1151. For example, the fiducial mark 127, guide groove 133 and sample tube holder 139 can be linearly aligned along a center of the slide channel 115. Such alignment can facilitate deposition of a sample on a slide in the slide channel 115 using a syringe as will be discussed. The slide preparation apparatus can be fabricated from plastics, polymers, metals, glass or other appropriate materials.

Figure 2A:
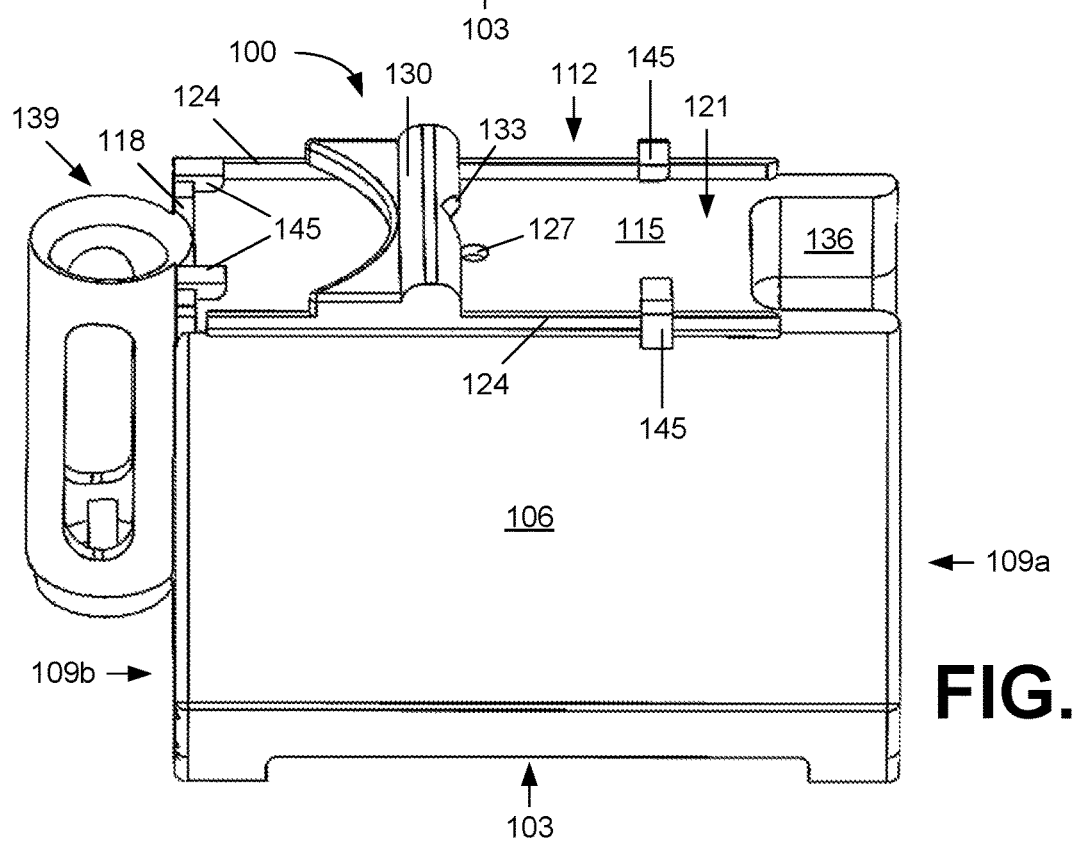
FIGS. 2A and 2B illustrate another example of a slide preparation apparatus, in accordance with various embodiments of the present disclosure.
Figure 2B:
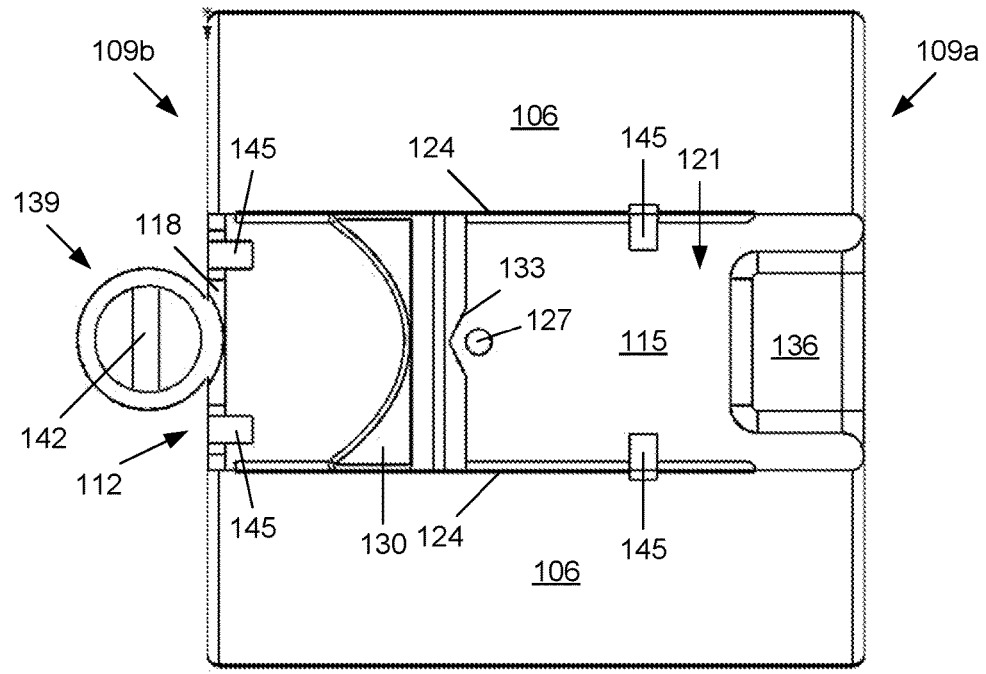

Referring next to FIGS. 2A and 2B, shown is another example of a slide preparation apparatus 100. As illustrated in FIGS. 2A and 2B, the stop 118 and/or sidewalls 124 of the slide channel 115 can include additional tabs or clips 145 that can aid in securing the slide in position in the slide channel 115. In addition, the sample tube holder 139 can include tapered edges to facilitate insertion of the sample tube into the cylindrical chamber.

Figure 3A:
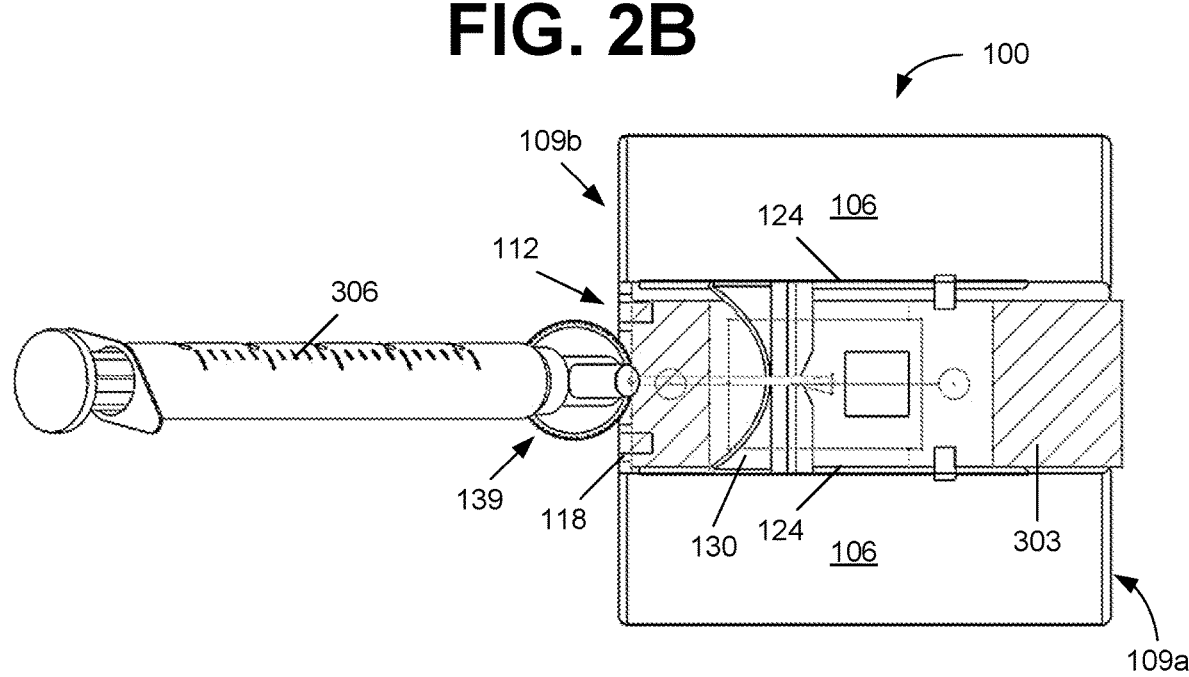
FIGS. 3A-3C illustrate an example of a syringe positioned on the slide preparation apparatus of FIGS. 2A and 2B for deposit of a sample on a slide, in accordance with various embodiments of the present disclosure.
Figure 3B:
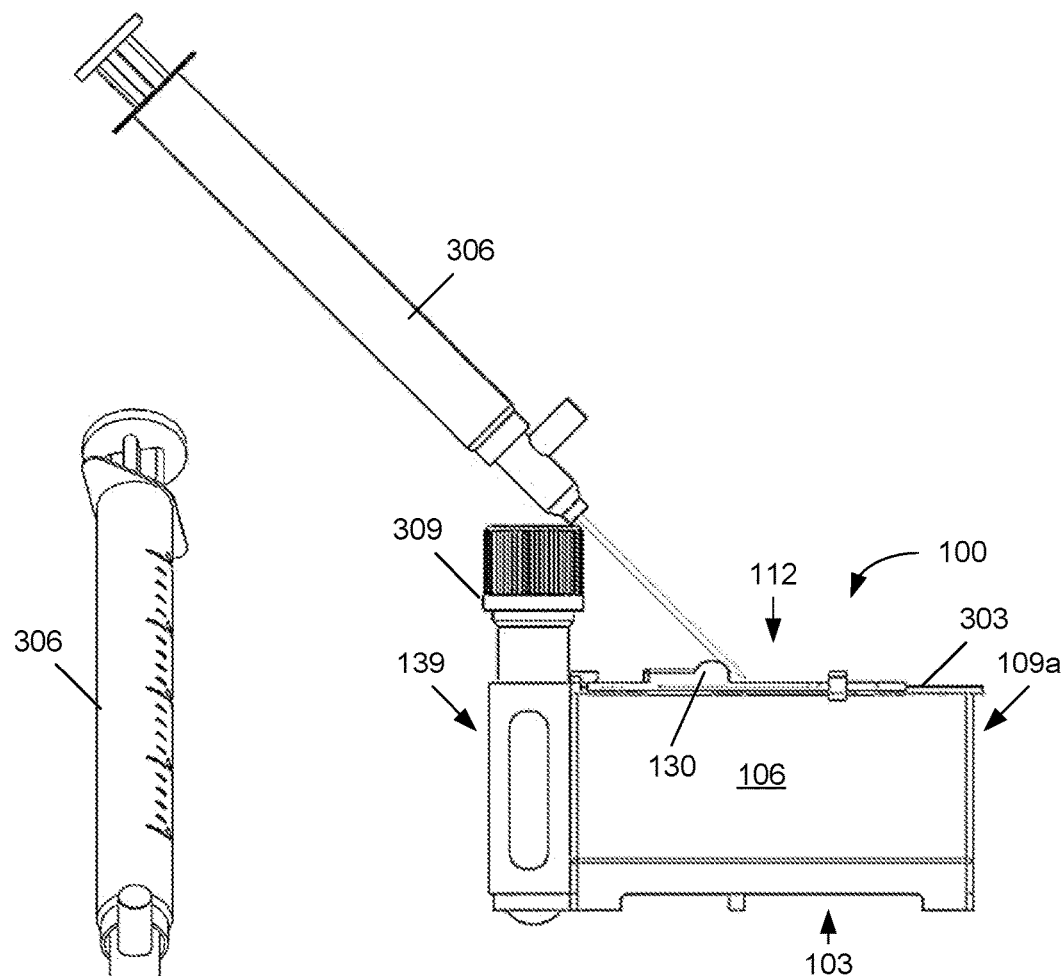
Figure 3C:
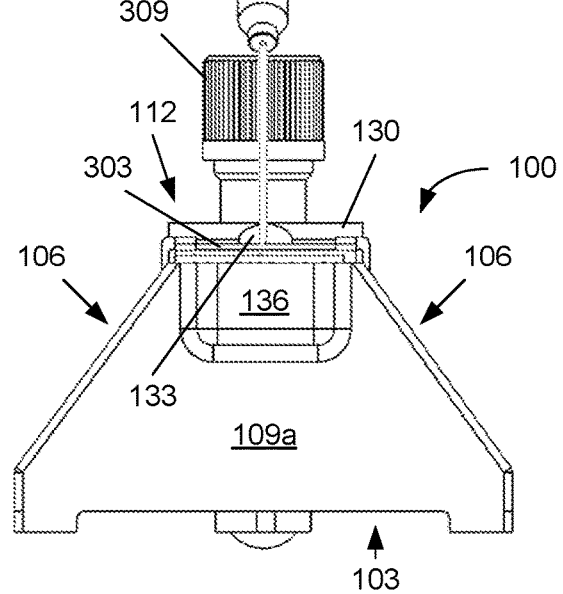

FIGS. 3A-3C illustrate the use of the slide preparation apparatus 100 of FIGS. 2A and 2B for placement of a sample on a slide. FIG. 3A is a top view illustrating a slide 303 secured in the slide channel 115 of the slide preparation apparatus 100. The slide 303 is inserted into the slide channel 115, under the support bar 130, until it engages with the stop 118. The support bar 130 and tabs or clips 145 on the stop 188 and sidewalls 124 hold the slide 303 in position in the slide channel 115. With the slide 303 in this position, the fiducial mark 127 indicates the location where the specimen should be deposited on the slide 303. The fiducial mark 127 can be seen through a transparent or semi-transparent slide 303 by the user to assist with placement of the sample. A syringe 306 containing the sample can be positioned as illustrated in FIGS. 3A-3C. As seen in the side view of FIG. 3B, the syringe 306 can be supported by a sample tube 309 inserted in the sample tube holder 139 and by the support bar 130. The sample can be extracted from the sample tube 309 prior to being positioned on the sample tube 309 or may be extracted from another sample tube or source. The sample can be extracted from the sample tube 309 before the sample tube 309 is inserted into the sample tube holder 139 or can be extracted from the sample tube 309 while it is located in the sample tube holder 139.

With the syringe 306 positioned on the sample tube 309 and the syringe needle in the guide groove 133 of the support bar 130, as shown in the end view of FIG. 3C, the end of the needle is located over the fiducial mark 127. The sample can be discharged from the syringe needle at the desired location on the slide 303. The alignment of the sample tube holder 139, guide groove 133 and fiducial mark 127 can significantly aid in the consistent placement of samples on slides 303 for processing. Once the sample has been deposited on the slide 303, the sample may be smeared or otherwise treated on the surface of the slide 303. The slide 303 with the sample can be removed from the slide preparation apparatus 100 by grasping the end of the slide 303 over the cavity 136 in the end surface 109a. The user can insert a finger or thumb under the slide 303 to grasp the slide 303 and pull it out of the slide channel 115.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The term "substantially" is meant to permit deviations from the descriptive term that don't negatively impact the intended purpose. Descriptive terms are implicitly understood to be modified by the word substantially, even if the term is not explicitly modified by the word substantially.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

The invention claimed is:

1. A slide preparation apparatus, comprising:
a base having an upper surface;
  a slide channel extending along the upper surface;
  a support bar having a first portion and a second portion, said bar extending across and slightly above the slide channel, the support bar including a guide groove notch, the guide groove notch partially separating the first and second portions of the support bar; and
a sample tube holder separate from the support bar and removably secured to an end surface of the slide preparation apparatus, the sample tube holder configured to secure a sample tube in a vertical position adjacent to the upper surface.

2. The slide preparation apparatus of claim 1, wherein the notch in the support bar is substantially V-shaped.

3. The slide preparation apparatus of claim 1, wherein the support bar includes a curved portion opposite of the notch.

4. The slide preparation apparatus of claim 1, further comprising a stop extending across a width of the slide channel.

5. The slide preparation apparatus of claim 4, wherein the width of the slide channel corresponds to a width of a slide.

6. The slide preparation apparatus of claim 1, wherein the slide channel comprises sidewalls on opposite sides of the slide channel, the sidewalls configured to constrain a slide therebetween.

7. The slide preparation apparatus of claim 3, further comprising a gap having a fixed distance between the curved portion of the support bar and the sample tube holder.

8. The slide preparation apparatus of claim 1, further comprising a fiducial mark, wherein the guide grove notch is on a side of the support bar adjacent to the fiducial mark.

9. The slide preparation apparatus of claim 4, wherein the stop extends substantially or entirely across the width of the slide channel.

10. The slide preparation apparatus of claim 8, wherein the fiducial mark defines a target location for deposition of a sample on a slide inserted in the slide channel.

11. The slide preparation apparatus of claim 1, wherein a top of the sample tube holder is positioned below the support bar.

12. The slide preparation apparatus of claim 1, wherein the notch partially surrounds an opening partially separating the first and second portions of the support bar, and the sample tube holder is detachably secured to the end surface of the slide preparation apparatus.

13. The slide preparation apparatus of claim 1, wherein the sample tube holder comprises a cylindrical chamber sized to receive a sample tube.

14. The slide preparation apparatus of claim 12, wherein the sample tube is a blood collection tube.

15. The slide preparation apparatus of claim 4, wherein the sample tube holder extends between the stop and a base of the apparatus.

16. The slide preparation apparatus of claim 4, further comprising a cavity at an end of the upper surface opposite the stop.

17. The slide preparation apparatus of claim 13, further comprising a support structure extending across an amount of the cylindrical chamber.

18. The slide preparation apparatus of claim 17, wherein the support structure extends about half the distance across the cylindrical chamber.

19. The slide preparation apparatus of claim 13, wherein the sample tube holder comprises at least one opening extending through a side of the cylindrical chamber.

20. The slide preparation apparatus of claim 1, further comprising a fiducial mark at the upper surface, wherein the guide groove notch is configured to receive a needle and align the needle with the fiducial mark.

* * * * *